United States Patent [19]

Sivik et al.

[11] Patent Number: 5,710,122
[45] Date of Patent: Jan. 20, 1998

[54] SULFONATE DERIVATIZED PERFUMES

[75] Inventors: Mark Robert Sivik, Fairfield; Frederick Anthony Hartman, Cincinnati, both of Ohio

[73] Assignee: The Procter & Gamble Company, Cincinnati, Ohio

[21] Appl. No.: 575,418

[22] Filed: Dec. 20, 1995

[51] Int. Cl.$^6$ .................................... A61K 7/46
[52] U.S. Cl. .................. 512/7; 424/76.1; 424/76.2; 424/76.21
[58] Field of Search .................. 512/7; 424/76.1, 424/76.2, 76.21

[56] References Cited

U.S. PATENT DOCUMENTS

| | | | |
|---|---|---|---|
| 2,035,494 | 3/1936 | Meuly | 512/7 |
| 3,779,932 | 12/1973 | Jaggers et al. | 512/7 |
| 4,187,251 | 2/1980 | Schlesppnik | 512/7 |
| 4,742,044 | 5/1988 | Boden | 512/7 |
| 5,366,665 | 11/1994 | Cho | 252/549 |
| 5,378,468 | 1/1995 | Suffis et al. | 424/401 |

*Primary Examiner*—James H. Reamer
*Attorney, Agent, or Firm*—R. S. Echler, Sr.; B. M. Bolam; K. W. Zerby

[57] ABSTRACT

The present invention relates to novel sulfonates based upon alcohol perfumes. The sulfonates have the general formulas of (I) and (II):

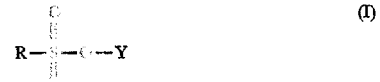

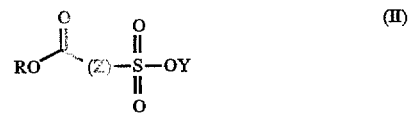

where R and Z are independently selected from the group consisting of nonionic or anionic, substituted or unsubstituted $C_1$–$C_{30}$ straight, branched or cyclic alkyl, alkenyl, alkynyl, alkylaryl or aryl group; Y is a radical that, upon hydrolysis of the sulfonate, forms an alcohol with a boiling point at 760 mm Hg of less than about 300° C. that is a perfume; and excluding geranyl and neryl methanesulfonates. Preferably these sulfonate compounds are incorporated into laundry and cleaning compositions.

17 Claims, No Drawings

SULFONATE DERIVATIZED PERFUMES

TECHNICAL FIELD

The present invention relates to novel sulfonates based upon alcohol perfumes. These sulfonate compounds are perfume alcohol derivatives, comprising a radical that upon hydrolysis forms an alcohol with a boiling point at 760 mm Hg of less than about 300° C. that is a perfume. Preferably these sulfonate compounds are incorporated into laundry and cleaning compositions.

BACKGROUND OF THE INVENTION

Consumer acceptance of cleaning and laundry products is determined not only by the performance achieved with these products but the aesthetics associated therewith. The perfume systems are therefore an important aspect of the successful formulation of such commercial products.

What perfume system to use for a given product is a matter of careful consideration by skilled perfumers. While a wide array of chemicals and ingredients are available to perfumers, considerations such as availability, cost, and compatibility with other components in the compositions limit the practical options. Thus, there continues to be a need for low-cost, compatible perfume materials useful for cleaning and laundry compositions.

It has been discovered that sulfonates of certain perfume alcohols are particularly well suited for laundry and cleaning compositions. In particular, it has been discovered that sulfonates of perfume alcohols will hydrolyze to give an alcohol perfume and the corresponding salt. In addition, hydrolyzable sulfonates of perfume alcohols provide release of the perfume over a longer period of time than by the use of the perfume itself in the laundry/cleaning compositions. Such materials therefore provide perfumers with more options for perfume ingredients and more flexibility in formulation considerations. These and other advantages of the present invention will be seen from the disclosures hereinafter.

BACKGROUND ART

Sulfonate chemistry is described more generally in March, ADVANCED ORGANIC CHEMISTRY, 4th Ed., pp. 352–353, 372, 404–405, 498–499 (John Wiley & Sons, N.Y.; 1992). Geranyl and neryl methanesulfonates are described as synthetic intermediates in Bunton, et al., *Cyclization and Allylic Rearrangement in Solvolyses on Monoterpenoids*, J. Org. Chem., Vol. 44, No. 18, pp. 3239 (1979).

SUMMARY OF THE INVENTION

The present invention relates to novel sulfonate compounds used to provide alternative means of perfume delivery for a wide variety of consumer products.

The novel sulfonates have the general formulas of (I) and (II):

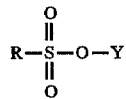

(I)

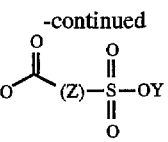

(II)

wherein R and Z are independently selected from the group consisting of nonionic or anionic, substituted or unsubstituted $C_1$–$C_{30}$ straight, branched or cyclic alkyl, alkenyl, alkynyl, alkylaryl or aryl group; Y is a radical that, upon hydrolysis of said sulfonate, forms an alcohol with a boiling point at 760 mm Hg of less than about 300° C. that is a perfume, and excluding geranyl and neryl methanesulfonates.

All percentages and ratios used herein are by weight of the total composition.

DETAILED DESCRIPTION OF THE INVENTION

The sulfonates have the general formulas (I) and (II):

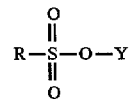

(I)

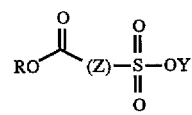

(II)

wherein R and Z are independently selected from the group consisting of nonionic or anionic, substituted or unsubstituted $C_1$–$C_{30}$ straight, branched or cyclic alkyl, alkenyl, alkynyl, alkylaryl or aryl group; Y is a radical that, upon hydrolysis of said sulfonate, forms an alcohol with a boiling point at 760 mm Hg of less than about 300° C. that is a perfume, and excluding geranyl and neryl methanesulfonates.

Preferably, R and Z are selected from the group consisting of substituted or unsubstituted $C_1$–$C_{20}$ straight, branched or cyclic alkyl, alkenyl, alkynyl, alkylaryl, aryl group or ring containing a herteroatom. Y is preferably a radical that upon hydrolysis of said sulfonate forms perfume alcohol selected from the group consisting of:

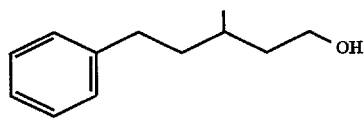

phenoxanol;

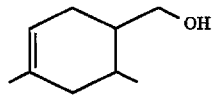

floralol;

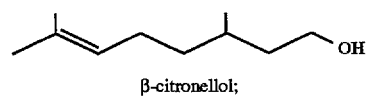

β-citronellol;

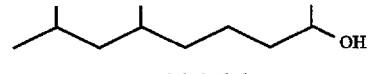

nonadyl alcohol;

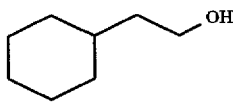

cyclohexyl ethanol;

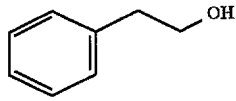

phenyl ethanol;

isoborneol;

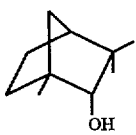

fenchol;

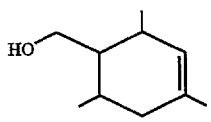

isocyclogeraniol;

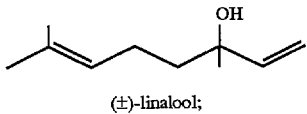

(±)-linalool;

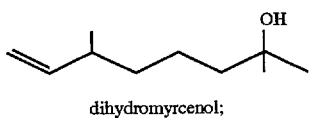

dihydromyrcenol;

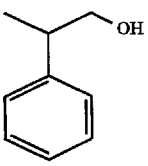

2-phenyl-1-propanol;

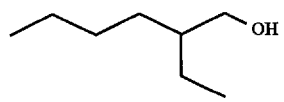

2-ethylhexanol;

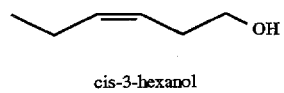

cis-3-hexanol

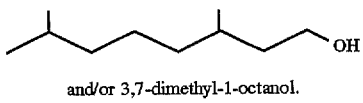

and/or 3,7-dimethyl-1-octanol.

The more preferred sulfonates are the p-toluenesulfonates (tosylates), 4-bromobenzenesulfonates (brosylates), and methanesulfonates (mesylates) of these alcohols. The most preferred sulfonates are the tosylates, brosylates, and mesylates of β-citronellol, phenoxanol, cis-3-hexenol, and phenyl ethanol.

Of course, one of ordinary skill in the art will recognize that other sulfonates satisfying the general formula (I) or (II) can also be employed in the present invention.

Methods of Manufacture

The following examples further describe and demonstrate embodiments within the scope of the present invention. The examples are given solely for the purpose of illustration and are not to be construed as limitations of the present invention, as many variations thereof are possible without departing from the spirit and scope of the invention. It is recognized that the materials used to prepare the sulfonates herein preferably should not have other materials present that would change the essential perfume character of the perfume alcohol.

EXAMPLE 1

Phenoxanyl p-toluenesulfonate

Phenoxanol (30.00 g, 0.168 mol) and pyridine (130 mL) are combined in a flask fitted with a condenser, internal thermometer, mechanical stirrer and argon inlet. The solution is cooled to −10° C. and to it is added p-toluenesulfonyl chloride (39.28 g, 0.202 mol) in portions via Gooch tubing so as to maintain the reaction temperature between −10°–0° C. After 3 h, water (20 mL) is added in portions so as to keep the temperature of the reaction below 5° C. The reaction mixture is warmed to room temperature and then poured into a separatory funnel containing 275 mL of ether. The layers are separated and the organic layer is washed with 5M $H_2SO_4$ (75 mL), saturated $CuSO_4$ solution (75 mL), water (2×75 mL) and saturated $NaHCO_3$ solution (75 mL). After drying over $MgSO_4$, the organic layer is filtered and concentrated to leave a light yellow liquid as phenoxanyl p-toluenesulfonate. Purity of the product is determined by thin layer chromatography and the structure confirmed by $^1H$ and $^{13}C$ NMR.

EXAMPLE 2

The procedure of Example 1 is repeated with the substitution of floralol; β-citronellol; nonadyl alcohol; cyclohexyl ethanol; phenyl ethanol; isoborneol; fenchol; isocyclogeranol; (±)-linalool; dihydromyrcenol; 2-phenyl-1-propanol; 2-ethylhexanol; cis-3-hexenol and/or 3,7-dimethyl-1-octanol for the phenoxanol.

EXAMPLE 3 b-Citronellyl p-toluenesulfonate b-Citronellol (21.05 g, 0.128 mol) and tetrahydrofuran (140 mL) are combined in a flask fitted with a condenser, internal thermometer, mechanical stirrer and argon inlet. The solution is cooled to −78° C. and to it is added n-butyllithium (56.3 mL, 0.141 mol, 2.5M in hexanes) via syringe. The mixture is stirred for 60 min before a solution of p-toluenesulfonyl chloride (39.28 g, 0.2019 mol) dissolved in 50 mL of tetrahydrofuran is added. After addition is complete, the mixture is stirred for 30 min at −78° C. and then at room temperature overnight. Ether (100 mL) is added and the mixture is quenched with water (100 mL). The organic layer is dried over MgSO$_4$, filtered and concentrated to leave a yellow-orange liquid. The oil is purified on silica gel eluting with 20% ethyl acetate in petroleum ether to give a light yellow liquid as b-citronellyl p-toluenesulfonate. Purity of the product is determined by thin layer chromatography and the structure confirmed by $^1$H and $^{13}$C NMR.

EXAMPLE 4

2-Ethylhexanyl p-toluenesulfonate

2-Ethylhexanol (50.51 g, 0.384 mol) and pyridine (260 mL) are combined in a flask fired with a condenser, internal thermometer, mechanical stirrer and argon inlet. The solution is cooled to −5° C. and to it is added p-toluenesulfonyl chloride (89.63 g, 0.416 mol) in portions via Gooch tubing so as to maintain the reaction temperature −5°–5° C. After 3 h, water (40 mL) is added in portions so as to keep the temperature of the reaction below 5° C. The reaction mixture is warmed to room temperature and then poured into a separatory funnel containing 540 mL of ether. The layers are separated and the organic layer is washed with 5M H$_2$SO$_4$ (2×140 mL), saturated CuSO4 solution (140 mL), water (2×140 mL) and saturated NaHCO3 solution (140 mL). After drying over MgSO4, the organic layer is filtered, and concentrated to leave a light yellow liquid as 2-ethyhexanyl p-toluenesulfonate. Purity of the product is determined by thin layer chromatography and the structure confirmed by 1H and 13C NMR.

EXAMPLE 5

2-Ethylhexanyl 4-bromobenzenesulfonate

The procedure for Example 3 is repeated with the substitution of 4 bromobenzenesulfonyl chloride for p-toluenesulfonyl chloride.

EXAMPLE 6

Phenoxanyl methanesulfonate

The procedure for Example 1 is repeated with the substitution of methanesulfonyl chloride for p-toluenesulfonyl chloride.

EXAMPLE 7

Phenoxanyl (phenoxylacetyl) sulfonate

The procedure for Example 1 is repeated with the substitution chlorosulfonylacetyl chloride for p-toluenesulfonyl chloride.

COMPOSITIONS

The present invention also relates to a composition for providing a prolonged scent signal to surfaces, comprising:

(A) an amount, effective to provide prolonged scent signal, of sulfonate derivatized perfume compound; and (B) an effective amount of a carrier material to deliver said compound to surfaces;

wherein the sulfonate defivatized perfume compound is selected from the group consisting of:

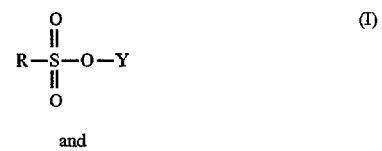

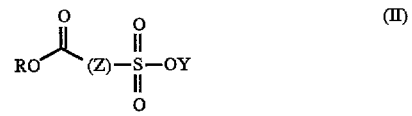

wherein R and Z are independently selected from the group consisting of nonionic or anionic, substituted or unsubstituted C$_1$–C$_{30}$ straight, branched or cyclic alkyl, alkenyl, alkynyl, alkyl aryl or aryl group; Y is a radical that, upon hydrolysis of said sulfonate, forms an alcohol with a boiling point at 760 mm Hg of less than about 300° C. that is a perfume, and excluding geranyl and neryl methanesulfonate.

Preferably, R and Z are selected from the group consisting of substituted or unsubstituted C$_1$–C$_{20}$ straight, branched or cyclic alkyl, alkenyl, alkynyl, alkylaryl, aryl group or ring containing a herteroatom. Y is preferably a radical that upon hydrolysis of said sulfonate forms perfume alcohol selected from the group consisting of phenoxanol; floralol; β-citronellol; nonadyl alcohol; cyclohexyl ethanol; phenyl ethanol; isoborneol; fenchol; isocyclogeranol; (±)-linalool; dihydromyrcenol; 2-phenyl-1-propanol; 2-ethylhexanol; cis-3-hexenol and/or 3,7-dimethyl-1-octanol.

The most preferred sulfonates are the p-toluenesulfonates (tosylates), 4-bromobenzenesulfonates (brosylates), and methanesulfonates (mesylates) of β-citronellol, phenoxanol, cis-3-hexenol, and phenyl ethanol.

The carrier and/or diluent employed in the instant compositions is a non-toxic, non-irritating substance which when mixed with the sulfonate derivatized perfume compound, promotes the deposition of said sulfonate derivatized perfume compound onto surfaces. The compositions of the present invention preferably comprise from about 25% to about 95%, preferably from about 50% to about 90% of a liquid carrier. Preferably the carrier and/or diluent is primarily water due to its low cost relative availability, safety, and environmental compatibility. The level of water in the liquid carrier is at least about 50%, preferably at least about 60%, by weight of the carrier. Mixtures of water and low molecular weight, e.g., <100 g/mol, organic solvent, e.g., lower alcohol such as ethanol, propanol, isopropanol or butanol are useful as the carrier liquid. Low molecular weight alcohols include monohydric, dihydric (glycol, etc.) trihydric (glycerol, etc.), and higher polyhydric (polyols) alcohols.

What is claimed is:

1. A sulfonate derivatized perfume compound, selected from the group consisting of sulfonates having the formula (I), and (II):

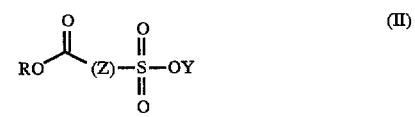

wherein R and Z are independently selected from the group consisting of nonionic or anionic, substituted or unsubstituted C$_1$–C$_{30}$ straight, branched or cyclic alkyl, alkenyl, alkynyl, alkylaryl or aryl group; Y is a radical that, upon hydrolysis of said sulfonate, forms an alcohol with a boiling point at 760 mm Hg of less than about 300° C. which are perfumes, and excluding geranyl and neryl methanesulfonate.

2. The sulfonate derivatized perfume compound of claim 1 wherein Y is a radical that upon hydrolysis of said sulfonate forms perfume alcohol selected from the group consisting of phenoxanol, floralol, β-citronellol, nonadol, cyclohexyl ethanol, phenyl ethanol, isoborneol, fenchol, isocyclogeraniol, (±)-linalool, dihydromyrcenol, 2-phenyl-1-propanol, 2-ethylhexanol, cis-3-hexenol, 3,7-dimethyl-1-octanol, and combinations thereof.

3. The sulfonate derivatized perfume compound as claimed in claim 2, wherein said sulfonate is selected from the tosylates, brosylates, and mesylates of said alcohol perfumes, and mixtures thereof.

4. The sulfonate derivatized perfume compound as claimed in claim 3 wherein said sulfonate is selected from the group of sulfonates derived from alcohol perfumes consisting of β-citronellol, phenoxanol, cis-3-hexenol, phenyl ethanol, and mixtures thereof.

5. The sulfonate derivatized perfume compound of claim 1 wherein said sulfonate is selected from the group consisting of the tosylates of Formula I.

6. The sulfonate derivatized perfume compound of claim 1 wherein said sulfonate is selected from the group consisting of the brosylates of Formula I.

7. The sulfonate derivatized perfume compound of claim 1 wherein said sulfonate is selected from the group consisting of the mesylates of Formula I.

8. The sulfonate derivatized perfume compound of claim 1 wherein said sulfonate is selected from the group consisting of the tosylates of Formula II.

9. The sulfonate derivatized perfume compound of claim 1 wherein said sulfonate is selected from the group consisting of the brosylates of Formula II.

10. The sulfonate derivatized perfume compound of claim 1 wherein said sulfonate is selected from the group consisting of the mesylates of Formula II.

11. A composition for providing a prolonged scent signal to surfaces, comprising:

(A) an amount, effective to provide prolonged scent signal, of sulfonate derivatized perfume compound of claim 1; and (B) an effective amount of a carrier material to deliver said compound to surfaces.

12. The composition for providing a prolonged scent signal to surfaces of claim 11 wherein said sulfonate is selected from the group consisting of the tosylates of Formula I.

13. The composition for providing a prolonged scent signal to surfaces of claim 11 wherein said sulfonate is selected from the group consisting of the brosylates of Formula I.

14. The composition for providing a prolonged scent signal to surfaces of claim 11 wherein said sulfonate is selected from the group consisting of the mesylates of Formula I.

15. The composition for providing a prolonged scent signal to surfaces of claim 11 wherein said sulfonate is selected from the group consisting of the tosylates of Formula II.

16. The composition for providing a prolonged scent signal to surfaces of claim 11 wherein said sulfonate is selected from the group consisting of the brosylates of Formula II.

17. The composition for providing a prolonged scent signal to surfaces of claim 11 wherein said sulfonate is selected from the group consisting of the mesylates of Formula II.

* * * * *